(12) United States Patent
Watai et al.

(10) Patent No.: US 7,041,820 B2
(45) Date of Patent: May 9, 2006

(54) PROCESS FOR PRODUCING (DIOXOLENON-4-YL)METHYL ESTER DERIVATIVE

(75) Inventors: Toshiyuki Watai, Takaoka (JP); Mitsuru Takase, Niigata (JP); Takahiro Sagae, Odawara (JP); Shigeo Mori, Niigata (JP); Noriaki Kawahara, Niigata (JP)

(73) Assignees: Nippon Soda Co., Ltd., Tokyo (JP); Daiichi Asubio Pharma Co., Ltd., Tokyo (JP)

( * ) Notice: Subject to any disclaimer, the term of this patent is extended or adjusted under 35 U.S.C. 154(b) by 28 days.

(21) Appl. No.: 10/473,297

(22) PCT Filed: Mar. 29, 2002

(86) PCT No.: PCT/JP02/03160

§ 371 (c)(1), (2), (4) Date: Feb. 18, 2004

(87) PCT Pub. No.: WO02/079185

PCT Pub. Date: Oct. 10, 2002

(65) Prior Publication Data

US 2004/0133016 A1    Jul. 8, 2004

(30) Foreign Application Priority Data

Mar. 30, 2001    (JP)    ............................ 2001-100561

(51) Int. Cl.
*C07D 499/08*    (2006.01)

(52) U.S. Cl. ................... 540/318; 205/215; 205/301; 205/302; 205/347

(58) Field of Classification Search ................ 549/229; 540/310, 205, 215, 301, 302, 347, 318
See application file for complete search history.

(56) References Cited

FOREIGN PATENT DOCUMENTS

JP    6-192270    7/1994

OTHER PUBLICATIONS

Yeh et al, J. of the Chinese Chemical Soc., vol. 38, p. 221-230 (1991).*
Weber et al, Phase Transfer Catalysis in Organic Chemistry, Springer-Verlag, Berlin, p. 1-15 and 85-95 (1977).*
Sakamoto et al. Studies on prodrugs. VI. Preparation and Characterization of . . . Esters of Mecillinam, Chem. Pharm. Bull., vol. 35, No. 2, pp. 642-646 (1987).
The Chemical Society of Japan, 4th Edit. Jikken Kagaku Koza 27, Seibutsu Yuki, Maruzen Co. Ltd. p. 251-253 (1991) and English Translation.
Tabuse and Nishitani (translators), "Sokan idou shokubai", 1st ed. (1978), Kagaku Dojin Publishing Co., p. 1-14 and 99-111) and English language Counterpart.

* cited by examiner

*Primary Examiner*—Bernard Dentz
(74) *Attorney, Agent, or Firm*—Paul E. White, Jr.; Manelli Denison & Selter PLLC

(57) ABSTRACT

There is provided a method by which various compounds (1) having a carboxyl group in the molecule have the carboxyl group converted to a (dioxolenon-4-yl)methyl ester at low cost, in a simple way and at high yield.

The process for producing compounds of formula (3) according to the reaction scheme shown below comprises reacting carboxylic acids of formula (1) with 4-chloromethyldioxolenone compounds of formula (2) in a solvent in the presence of both a phase transfer catalyst and a metal iodide:

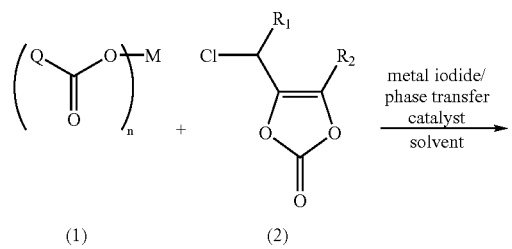

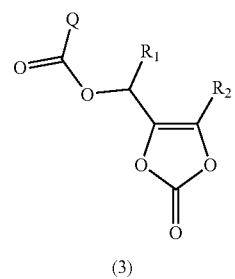

[where Q represents an organic group, M represents a hydrogen atom, an alkali metal, an alkaline earth metal or a transition metal, $R_1$ and $R_2$ represent a hydrogen atom, an optionally substituted ($C_{1-6}$ alkyl group or phenyl group)].

12 Claims, No Drawings

PROCESS FOR PRODUCING (DIOXOLENON-4-YL)METHYL ESTER DERIVATIVE

This application is a national stage entry of PCT/JP02/03160 filed Nov. 29, 2002.

TECHNICAL FIELD

This invention relates to a process by which (dioxolenon-4-yl)methyl ester derivatives useful as medicines, agrichemicals, etc. can be produced in industrial scale advantageously.

PRIOR ART

Heretofore, compounds represented by formula (4)

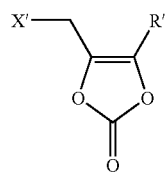

(where R' represents a hydrogen atom or an optionally substituted alkyl group, etc., and X' represents a halogen atom) have commonly been used as the starting material in a process by which compounds having a carboxyl group in the molecule (hereunder referred to as "carboxylic acids") are treated to have the carboxyl group converted to a (dioxolenon-4-yl)methyl ester.

An exemplary method currently known to be used in converting the carboxyl group in carboxylic acids to a (dioxolenon-4-yl)methyl ester is by employing 4-bromomethyl-5-methyldioxolenone as set forth below (see, for example, U.S. Pat. No. 4,448,732):

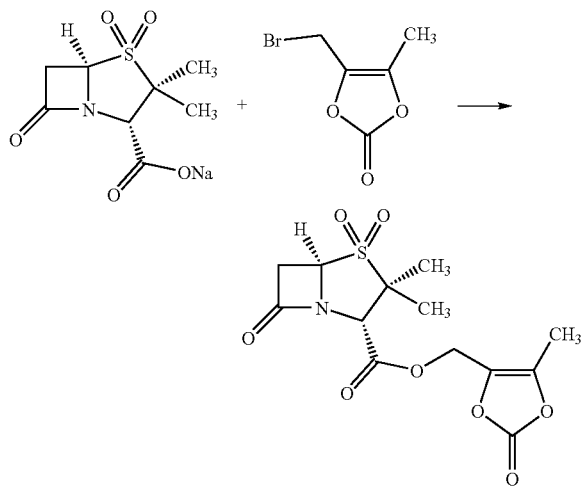

Using the highly reactive 4-bromomethyldioxolenone compound, the method produces the desired compound in comparatively high yield. However, this approach of using the 4-bromomethyl compound is not very advantageous for industrial mass production since the 4-bromomethyldioxolenone compound has poor chemical stability and is comparatively high in cost.

On the other hand, a 4-chloromethyldioxolenone compound is known to be more chemically stable than the 4-bromomethyldioxolenone compound and also easy to obtain. However, even if this compound is subjected to reaction under the same conditions as when the 4-bromomethyldioxolenone compound is reacted, efficient conversion to a (dioxolenon-4-yl)methyl ester cannot be realized.

The present invention has been accomplished under these circumstances and has as an object providing a process by which various compounds having a carboxyl group in the molecule can be treated to have the carboxyl group converted to a (dioxolenon-4-yl)methyl ester in a simple way and at high yield using the 4-chloromethyldioxolenone compound.

DISCLOSURE OF THE INVENTION

To attain the stated object, the present inventors conducted intensive studies and found that the reaction for conversion to a (dioxolenon-4-yl)methyl ester proceeded efficiently by reacting a carboxylic acid of formula (1) with a 4-chloromethyldioxolenone compound of formula (2) in a suitable solvent in the presence of both a phase transfer catalyst and a metal iodide. The present invention has been accomplished on the basis of this finding.

Thus, according to a first aspect of the invention, there is provided a process for producing a (dioxolenon-4-yl)methyl ester derivative of formula (3)

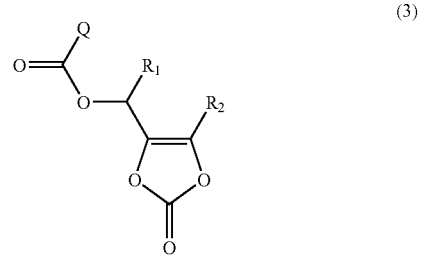

(where Q represents an organic group, and $R_1$ and $R_2$ each independently represent a hydrogen atom, an optionally substituted $C_{1-6}$ alkyl group or an optionally substituted phenyl group, provided that $R_1$ and $R_2$ may combine to form an optionally substituted ring having 3–8 carbon atoms) by reacting a carboxylic acid of formula (1)

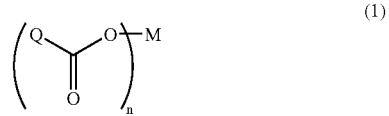

(where Q has the same meaning as defined above, M represents a hydrogen atom, an alkali metal, an alkaline earth metal or a transition metal, and n represents the atomic valency of M) with a 4-chloromethyldioxolenone compound of formula (2)

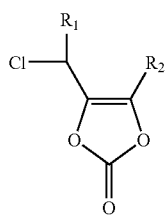

(2)

(where $R_1$ and $R_2$ have the same meanings as defined above) in a solvent in the presence of both a phase transfer catalyst and a metal iodide.

According to a second aspect of the invention, there is provided a process for producing a (dioxolenon-4-yl)methyl ester derivative of formula (3)

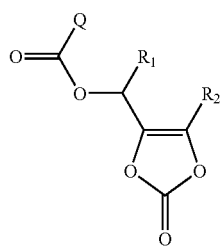

(3)

(where Q represents an organic group, and $R_1$ and $R_2$ each independently represent a hydrogen atom, an optionally substituted $C_{1-6}$ alkyl group or an optionally substituted phenyl group, provided that $R_1$ and $R_2$ may combine to form an optionally substituted ring having 3–8 carbon atoms) by reacting a carboxylic acid of formula (5)

(5)

(where Q has the same meaning as defined above) with a 4-chloromethyldioxolenone compound of formula (2)

(2)

(where $R_1$ and $R_2$ have the same meanings as defined above) in a solvent in the presence of both a quaternary ammonium hydroxide of the formula: $R_aR_bR_cR_d$NOH (where $R_a$–$R_d$ each independently represent a $C_{1-20}$ alkyl group or a $C_{7-20}$ aralkyl group) and a metal iodide.

In the invention, a polar solvent is preferably used as said solvent.

In the invention, said metal iodide is preferably used in an amount of 5–20 mol % of the 4-chloromethyldioxolenone compound of said formula (2) and it is also preferred to use an alkali metal iodide as said metal iodide.

Further in the invention, a quaternary ammonium salt is preferably used as said phase transfer catalyst and it is more preferred to use a benzyltrialkylammonium halide.

The invention can be applied with particular preference in a case of producing a compound among the (dioxolenon-4-yl)methyl ester derivatives of said formula (3) in which said Q is a fused heterocyclic group having a β-lactam ring.

It is also preferred in the invention that a base is further added at least in an amount corresponding to the amount of acidic impurities contained in the 4-chloromethyldioxolenone compound used which is represented by said formula (2).

It is also preferred in the invention that the reaction is performed by elevating the reaction temperature through a plurality of stages, and more preferably the reaction is performed by elevating the reaction temperature in two stages, the first stage at 40° C. or below and the second stage at 50° C. or above.

In the invention, the 4-chloromethyldioxolenone compound which features comparatively high chemical stability and easy availability is used, and it is characterized by adding a phase transfer catalyst and a metal iodide to the reaction system. According to the invention, the carboxyl group can be converted to a (dioxolenon-4-yl)methyl ester in a simple way and at high yield.

The present invention will now be described below in detail.

The invention provides a process for producing the (dioxolenon-4-yl)methyl ester compound of formula (3) by reacting the carboxylic acid of formula (1) with the compound of formula (2) in a solvent in the presence of both a metal iodide and a phase transfer catalyst as depicted in the following reaction scheme:

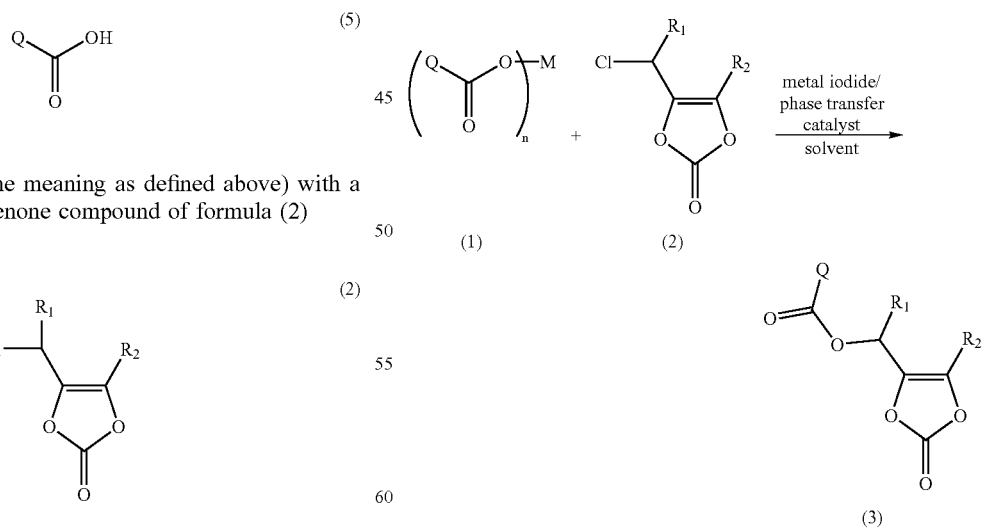

1) Compound of Formula (1)

In formula (1), Q represents an organic group. The term "organic group" means a functional group composed of several constituent elements including carbon atoms. Specific examples include: $C_{1-6}$ alkyl groups such as methyl, ethyl, n-propyl, isopropoyl, n-butyl, sec-butyl, t-butyl, n-pentyl and n-hexyl groups that may optionally be substituted by $G^1$; $C_{2-6}$ alkenyl groups such as ethenyl, n-propenyl, isopropenyl, n-butenyl, sec-butenyl, t-butenyl, n-pentenyl and n-hexenyl groups that may optionally be substituted by $G^1$; $C_{2-6}$ alkynyl groups such as ethynyl, n-propynyl, isopropynyl, n-butynyl, sec-butynyl, t-butynyl, n-pentynyl and n-hexynyl groups that may optionally be substituted by $G^1$; a phenyl group that may optionally be substituted by $G^1$; naphthyl groups such as α-naphthyl and β-naphthyl groups that may optionally be substituted by $G^1$; aralkyl groups such as benzyl, 2-phenylethyl, α-methylbenzyl and 3-phenylpropyl groups that may optionally be substituted by $G^1$; and heterocyclic groups that may optionally be substituted by $G^1$.

Said heterocyclic groups that may optionally be substituted by $G^1$ may be monocyclic or fused. Specific examples of monocyclic heterocyclic groups include (A) 5-membered saturated heterocyclic groups, (B) 5-membered unsaturated heterocyclic groups, (C) 6-membered saturated heterocyclic groups and (D) 6-membered unsaturated heterocyclic groups, as listed below.

(A) 5-Membered Saturated Heterocyclic Groups

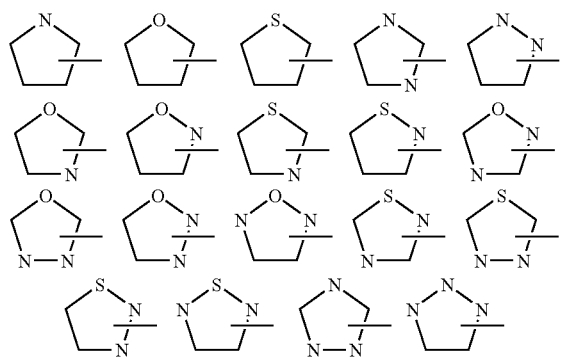

(B) 5-Membered Unsaturated Heterocyclic Groups

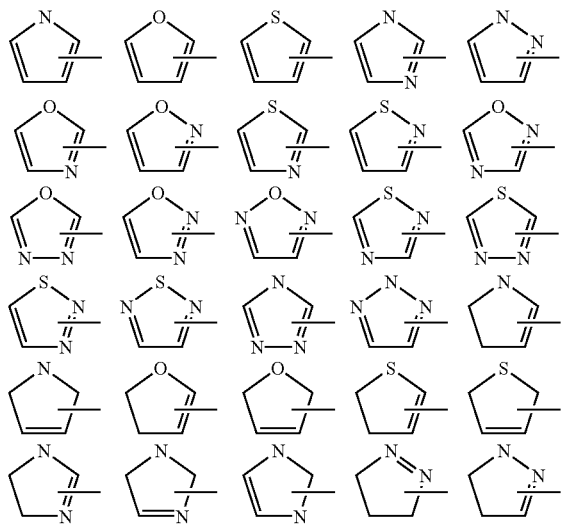

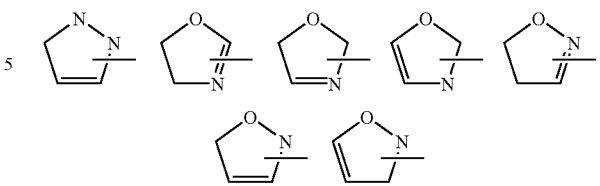

(C) 6-Membered Saturated Heterocyclic Groups

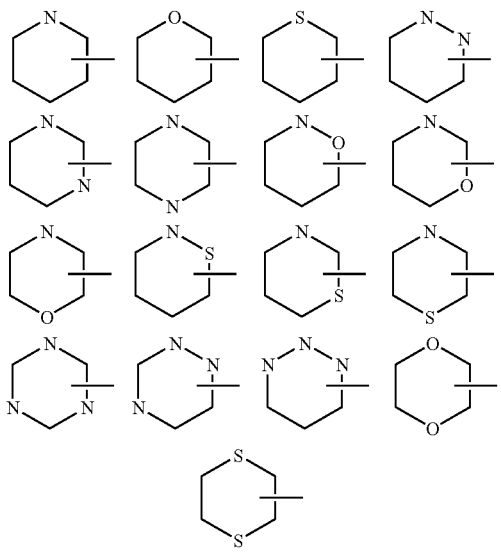

(D) 6-Membered Unsaturated Heterocyclic Groups

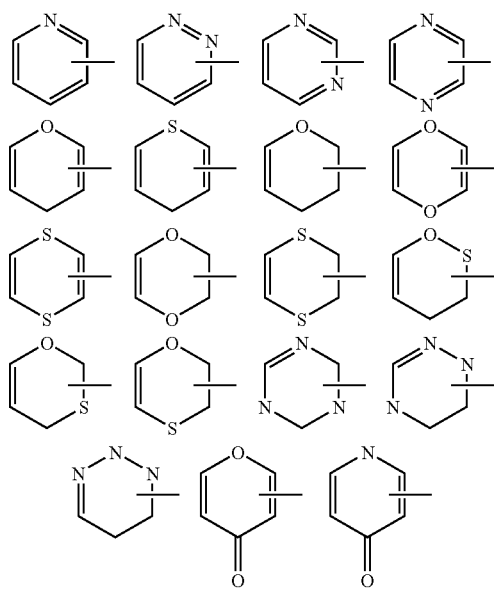

Exemplary fused heterocyclic groups include the following fused heterocyclic groups having a β-lactam ring which provide a base skeleton for β-lactam antimicrobial agents:

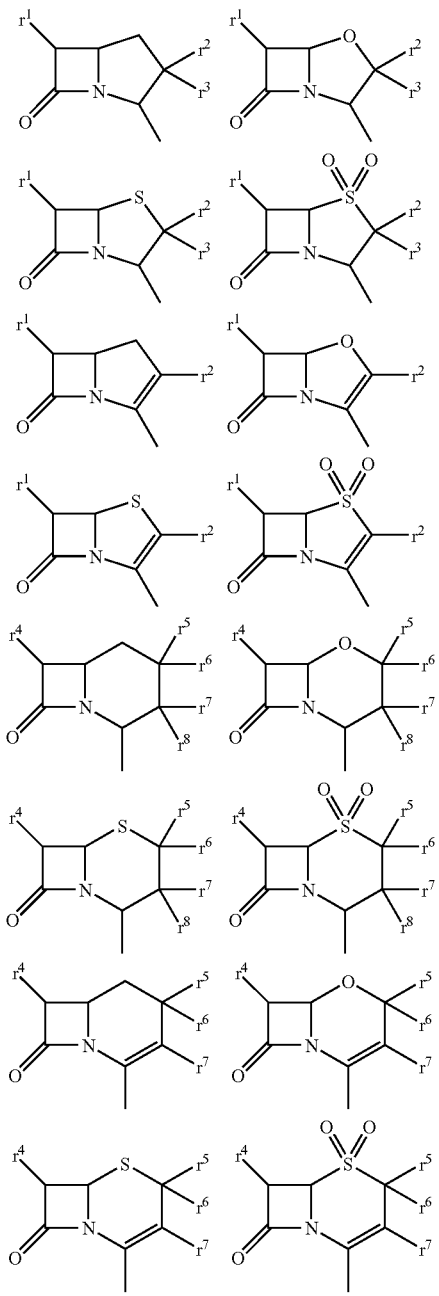

(where $r^1$ and $r^4$ represent a 1-hydroxyethyl group or an optionally substituted benzoylamino group; $r^2$, $r^5$, $r^6$, $r^7$ and $r^8$ each independently represent hydrogen or $C_{1-6}$ alkyl groups such as methyl, ethyl, n-propyl, isopropyl, n-butyl, sec-butyl, t-butyl, n-pentyl and n-hexyl groups that may optionally be substituted by $G^1$; $C_{2-6}$ alkenyl groups such as ethenyl, n-propenyl, isopropenyl, n-butenyl, sec-butenyl, t-butenyl, n-pentenyl and n-hexenyl groups that may optionally be substituted by $G^1$; $C_{2-6}$ alkynyl groups such as ethynyl, n-propynyl, isopropynyl, n-butynyl, sec-butynyl, t-butynyl, n-pentynyl and n-hexynyl groups that may optionally be substituted by $G^1$; tetrahydrofuranyl and heterocyclic groups that may optionally be substituted by $G^1$);

quinolinyl groups such as quinolin-2-yl, quinolin-3-yl, quinolin-4-yl, quinolin-5-yl, quinolin-6-yl, quinolin-7-yl and quinolin-8-yl groups;

isoquinolinyl groups such as isoquinolin-2-yl, isoquinolin-3-yl, isoquinolin-4-yl, isoquinolin-5-yl, isoquinolin-6-yl, isoquinolin-7-yl and isoquinolin-8-yl grouops.

In addition, $G^1$ represents the following: a nitro group; a cyano group; halogen atoms such as fluorine, chlorine, bromine and iodine; $C_{1-6}$ alkoxy groups such as methoxy, ethoxy, n-propoxy, isopropoxy, n-butoxy, sec-butoxy and t-butoxy groups; $C_{1-6}$ alkylthio groups such as methylthio, ethylthio, n-propylthio, isopropylthio, n-butylthio, sec-butylthio and t-butylthio groups; $C_{1-6}$ alkylsulfinyl groups such as methylsulfinyl, ethylsulfinyl, n-propylsulfinyl, isopropylsulfinyl, n-butylsulfinyl, sec-butylsulfinyl and t-butylsulfinyl groups; $C_{1-6}$ alkylsulfonyl groups such as methylsulfonyl, ethylsulfonyl, n-propylsulfonyl, isopropylsulfonyl, n-butylsulfonyl, sec-butylsulfonyl and t-butylsulfonyl groups; $C_{1-6}$ alkylamino groups such as methylamino, ethylamino and n-propylamino groups; di-$C_{1-6}$ alkylamino groups such as dimethylamino, diethylamino, dipropylamino, ethylmethylamino and methylpropylamino groups; $C_{1-6}$ alkylcarbonyl groups such as acetyl and propionyl groups; $C_{1-6}$ alkoxycarbonyl groups such as methoxycarbonyl, ethoxycarbonyl, n-propoxycarbonyl, isopropoxycarbonyl, n-butoxycarbonyl and t-butoxycarbonyl groups; an optionally $G^2$ substituted phenylsulfinyl group; an optionally $G^2$ substituted phenylsulfonyl group; or an optionally $G^2$ substituted phenylthio group.

$G^2$ represents the following: halogen atoms such as fluorine, chlorine and bromine; $C_{1-6}$ alkyl groups such as methyl, ethyl, n-propyl, isopropyl, n-butyl, sec-butyl and t-butyl groups; $C_{1-6}$ haloalkyl groups such as trifluoromethyl, 2,2,2-trifluoroethyl and pentafluoroethyl groups; or $C_{1-6}$ haloalkoxy groups such as trifluoromethoxy, 2,2,2-trifluoroethoxy and pentafluoroethoxy groups.

M typically represents the following: a hydrogen atom; alkali metals such as lithium, sodium and potassium; alkaline earth metals such as magnesium and calcium; or transition metals such as copper(I), copper(II), cobalt(II), cobalt(III), iron(II), iron(III), zinc(II) and manganese(II).

Among the carboxylic acids represented by formula (1), those compounds wherein Q is a heterocyclic group having a β-lactam ring have the β-lactam ring and asymmetric carbon atoms in the molecule, so racemization and decomposition reactions may potentially occur if conversion to (dioxolenon-4-yl)methyl ester is effected under hostile reaction conditions.

According to the invention, reactions can be caused to proceed under extremely mild conditions, so it can be applied with particular preference to the manufacture of β-lactam antimicrobial agents having a (dioxolenon-4-yl)methyl ester moiety.

Many of the compounds represented by said formula (1) are known substances and can be produced and made available by known methods.

2) Compound of Formula (2)

In said formula (2), $R_1$ and $R_2$ each independently represent a hydrogen atom, an optionally substituted $C_{1-6}$ alkyl group such as a methyl, ethyl, n-propyl, isopropyl, n-butyl, sec-butyl, t-butyl, n-pentyl or n-hexyl group, or an optionally substituted phenyl group.

Examples of the substituent on said $C_{1-6}$ alkyl group and phenyl group include the following: a nitro group; a cyano group; a halogen atom such as fluorine, chlorine, bromine or iodine; $C_{1-6}$ alkoxy groups such as methoxy, ethoxy, n-propoxy, isopropoxy, n-butoxy and t-butoxy groups; $C_{1-6}$ alkylthio groups such as methylthio, ethylthio, n-propylthio, isopropylthio, n-butylthio and t-butylthio groups; $C_{1-6}$ alkylsulfinyl groups such as methylsulfinyl and ethylsulfinyl groups; $C_{1-6}$ alkylsulfonyl groups such as methylsulfonyl, ethylsulfonyl, n-propylsulfonyl, isopropylsulfonyl, n-butylsulfonyl and t-butylsulfonyl groups; $C_{1-6}$ alkylamino groups such as methylamino, ethylamino and n-propylamino groups; di-$C_{1-6}$ alkylamino groups such as dimethylamino and diethylamino groups; $C_{1-6}$ alkylcarbonyl groups such as acetyl and propionyl groups; $C_{1-6}$ alkoxycarbonyl groups such as methoxycarbonyl and ethoxycarbonyl groups; an optionally $G^3$ substituted phenylsulfinyl group, an optionally $G^3$ substituted phenylsulfonyl group and an optionally $G^3$ substituted phenylthio group.

Examples of said $G^3$ include: halogen atoms such as fluorine, chlorine and bromine; $C_{1-6}$ alkyl groups such as methyl and ethyl groups; $C_{1-6}$ haloalkyl groups such as a trifluoromethyl group; and $C_{1-6}$ haloalkoxy groups such as a trifluoromethoxy group.

If desired, $R_1$ and $R_2$ may combine to form an optionally substituted ring having 3–8 carbon atoms. Examples of the ring having 3–8 carbon atoms include cyclopentene, cyclohexene, cycloheptene and cyclooctene. Exemplary substituents on said ring include: $C_{1-6}$ alkyl groups such as methyl and ethyl groups; $C_{1-6}$ alkoxy groups such as methoxy, ethoxy, n-propoxy, isopropoxy, n-butoxy and t-butoxy groups; halogen atoms such as fluorine and chlorine;

$C_{1-6}$ alkylthio groups such as methylthio and ethylthio groups; substituted amino groups such as dimethylamino and acetylamino groups; a nitro group; and a cyano group. Said ring may have identical or different substituents in any positions.

Among the atoms or groups mentioned above, a hydrogen atom or a methyl group is particularly preferred as $R_1$ and $R_2$.

The following are preferred specific examples of the dioxolenone compound represented by said formula (2):

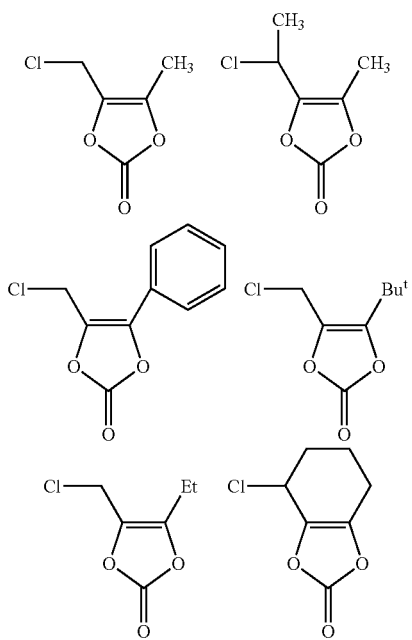

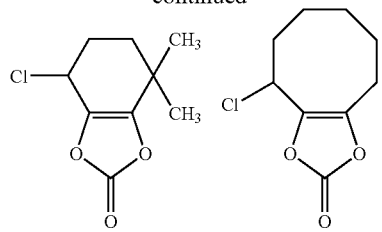

The dioxolenone compounds of the aforementioned formula (2) can be produced and made available, typically by the method described in U.S. Pat. No. 4,448,732.

The 4-chloromethyldioxolenone compound represented by said formula (2) is typically used in an amount of 1 mole to 10 moles, preferably in a range of 1 mole to 5 moles, per mole of the compound of formula (1).

3) Metal Iodide

Metal iodides are employed in the present invention. They are added in order to ensure that reactions proceed smoothly.

Exemplary metal iodides that can be employed in the reaction include: alkali metal iodides such as potassium iodide and sodium iodide; alkaline earth metal iodides such as magnesium iodide and calcium iodide; iodine salts of quaternary ammonium such as tetramethylammonium iodide, tetraethylammonium iodide, tetrapropylammonium iodide, tetrabutylammonium iodide, triethylmethylammonium iodide, benzyltrimethylammonium iodide and benzyl-tri-n-butylammonium iodide. These iodides may be used either alone or in admixture of two or more kinds as exemplified by potassium iodide/iodine and sodium iodide/iodine.

Among those, the use of alkali metal iodides is preferred from the viewpoints of easy availability, production cost, and high yield at which the desired product can be obtained.

The iodides are typically used in amounts of 0.1 to 40 mol %, preferably in the range of 5–20 mol %, relative to the compound of formula (1).

4) Phase Transfer Catalyst

In the present invention, a phase transfer catalyst is employed in addition to said metal iodide. A phase transfer catalyst is added to ensure smooth progress of the reaction.

As the phase transfer catalyst, quaternary ammonium salts, phosphonium salts, crown ethers and so forth are employed. Exemplary quaternary ammonium salts include: tetraalkylammonium chlorides such as tetramethylammonium chloride, tetraethylammonium chloride, tetrapropylammonium, chloride and tetrabutylammonium chloride (TBAC); tetraalkylammonioum bromides such as tetramethylammonium bromide, tetraethylammonium bromide, tetrapropylammonium bromide and tetrabutylammonium bromide; benzyltrialkylammonium halides such as benzyltrimethylammonium chloride, benzyltrimethylammonium bromide, benzyl-tri-n-butylammonium chloride (BTBAC) and benzyl-tri-n-butylammonium bromide; cetyltrialkylammonium halides such as cetyltrimethylammonium chloride, cetyltrimethylammonium bromide, cetyltriethylammonium chloride and cetyltriethylammonium bromide; tetraalkylammonium hydroxides such as tetramethylammonium hydroxide, tetraethylammonium hydroxide, tetrapropylammonium hydroxide and tetrabutylammonium hydroxide; and benzyltrialkylammonium hydroxides such as benzyltrimethylammonium hydroxide, benayltrimethylammonium hydroxide, benzyltri-n-butylammonium hydroxide and benzyl-tri-n-butylammonium hydroxide.

Exemplary phosphonium salts include phosphonium chloride, phosphonium bromide, trimethylphosphonium chloride, triethylphosphonium bromide, tetramethylphosphonium chloride, tetramethylphosphonium bromide and phosphonium iodide.

Exemplary crown ethers include 18-crown-6.

Among those, the use of quaternary ammonium salts is preferred from the viewpoints of easy availability, and high yield at which the desired product can be obtained. The use of tetraalkylammonium halides and benzyltrialkylammonium halides is more preferred, with the use of benzyltrialkylammonium halides being particularly preferred.

The phase transfer catalyst is typically employed in amounts ranging from 0.0001 mole to 1 mole per mole of the compound of formula (1).

5) Solvent

The solvents to be used in the invention are preferably those which can dissolve salts of the compound of said formula (1) as well as the reaction product, and examples are ether-, halogen-, nitrile-, amide-, ketone-, alcohol- and ester-based solvents.

Specific examples include: ether-based solvents such as diethyl ether, tetrahydrofuran (THF), 1,2-diomethoxyethane and 1,4-dioxane; halogen-based solvents such as dichloromethane, chloroform, trichloromethane, carbon tetrachloride and 1,2-dichloroethane; nitrile-based solvents such as acetonitrile and benzonitrile; phosphoric amide-based solvents such as hexamethylphosphoric triamide; amide-based solvents such as N,N-dimethylformamide (DMF), N,N-dimethylacetamide, 1,3-dimethylimidazolidine, 1,3-dimethyl-2-imidazolidinone and N-methylpyrrolidone; ketone-based solvents such as acetone, methyl ethyl ketone, methyl isobutyl ketone and cyclohexanone; alcohol-based solvents such as methanol, ethanol, n-propanol and isopropanol; ester-based solvents such as methyl acetate, ethyl acetate and n-propyl acetate; polar solvents such as dimethyl sulfoxide (DMSO) and water. These solvents can be used either alone or in admixture of two or more kinds.

Among these, the use of polar organic solvents is preferred since upon addition of water, the reaction mixture separates into layers, making it possible to wash the reaction mixture with water; the use of THF, DMF, DMSO or acetone is more preferred, and the use of THF is particularly preferred.

6) Base

In the present invention, if M in said formula (1) is a hydrogen atom (i.e. in the case of a carboxylic acid), a base is preferably added to the reaction system. Examples of useful bases include: alkali metal hydroxides such as sodium hydroxide and potassium hydroxide; alkaline earth metal hydroxides such as magnesium hydroxide and calcium hydroxide; alkali metal carbonates such as sodium carbonate and potassium carbonate; alkali metal hydrogencarbonates such as sodium hydrogencarbonate and potassium hydrogencarbonate; alkaline earth metal carbonates such as magnesium carbonate and calcium carbonate; metal hydrides such as sodium hydride and calcium hydride; metal alkoxides such as sodium methoxide, sodium ethoxide, potassium t-butoxide, magnesium methoxide and magnesium ethoxide; organic bases such as triethylamine, diisopropylethylamine, pyridine, 1,4-diazabicyclo[2,2,2]octane, 4-dimethylaminopyridine, 1,4-diazabicyclo[5,4,0]und-7-ene, n-butyl-lithium and lithium diisopropylamide; quaternary ammonium hydroxides represented by the formula: $R_aR_bR_cR_dNOH$.

Among those, the use of quaternary ammonium hydroxides represented by the formula: $R_aR_bR_cR_dNOH$ is particularly preferred since they serve the role of the base and the phase transfer catalyst.

Said $R_a$–$R_d$ each independently represent $C_{1-20}$ alkyl groups such as methyl, ethyl, n-propyl, isopropyl, n-butyl, isobutyl, sec-butyl, t-butyl, n-pentyl, neopentyl, n-hexyl, n-heptyl, n-octyl, n-nonyl, n-decyl, n-dodecyl and n-cetyl groups; or $C_{7-20}$ aralkyl groups such as benzyl, 3-chlorobenzyl, 4-methylbenzyl, 2-methoxybenzyl, α-methylbenzyl, 2-phenylethyl, 3-phenylpropyl and 4-phenyl-n-butyl groups.

Specific examples of the quaternary ammonium hydroxide represented by said formula: $R_aR_bR_cR_dNOH$ include: tetraalkylammonium hydroxides such as tetramethylammonium hydroxide, tetraethylammonium hydroxide, tetrapropylammonium hydroxide and tetrabutylammonium hydroxide; benzyltrialkyl hydroxides such as benzyltrimethylammonium hydroxide, benzyltrimethylammonium hydroxide, benzyltri-n-butyloammonium hydroxide and benzyl-tri-n-butyloammonium hydroxide.

The base is used typically in amounts ranging from 1 mole to 3 moles per mole of the compound of formula (1).

The 4-chloromethyldioxolenone compound represented by said formula (2) is relatively stable compared to the 4-bromomethyldioxolenone compound but if it is used industrially in large volumes, part of it will decompose, sometimes coming to contain acidic impurities. Therefore, in the present invention, in order to neutralize the acidic impurities contained in the 4-chloromethyldioxolenone compound represented by said formula (2) which is used in the reaction, it is preferred to further add a base to the reaction mixture at least in an amount corresponding to the amount of said acidic impurities.

Exemplary bases that can be used here include: alkali metal hydroxides such as sodium hydroxide and potassium hydroxide; alkaline earth metal hydroxides such as magnesium hydroxide and calcium hydroxide; alkali metal carbonates such as sodium carbonate and potassium carbonate; alkaline earth metal carbonates such as magnesium carbonate and calcium carbonate; hydrogencarbonates such as sodium hydrogencarbonate and potassium hydrogencarbonate; organic bases such as triethylamine and pyridine.

The reaction temperature for use in the production method of the invention is not limited to any particular value as long as it is within the temperature range where the compounds of formulas (1) and (2) or the compound of formula (3), which is the product, will not be decomposed in the reaction system using the above-mentioned reagents. A typical reaction temperature is 80° C. or less and it is preferred to perform the reaction at 60° C. or less.

If the compound of formula (1) has reactive points other than the carboxylic acid residue that react with formula (2) and if the reaction temperature is set on the higher side of the above-mentioned temperature range in consideration of the reaction efficiency, the progress of esterification is sometimes accompanied by simultaneous formation of by-products as the result of reaction at those other reaction points. Considering the drop in the yield of reaction and the increase in the complexity of separation steps due to increased impurities, it is preferable from an industrial point of view to minimize the formation of by-products. Thus, it is preferable to elevate the reaction temperature through a plurality of stages. Specifically, the reaction is first performed for a given time at low temperature, which is later elevated to a higher temperature where the reaction is further carried out for a certain period of time, whereby the reaction efficiency can be enhanced while suppressing the generation of by-products. Stated more specifically, the reaction temperature is elevated in two stages, the first stage being at 40° C. or less and the second stage at 50° C. or more. Particularly in the case where Q in formula (1) is a fused heterocyclic group having a β-lactam ring which is the basic skeleton of β-lactam antimicrobial agents, the reaction temperature is preferably controlled as described above.

After the end of the reaction, the desired product can be obtained by performing isolation and purification in accordance with ordinary techniques in organic synthetic chemistry. The structure of the desired product can be determined by, for example, measuring various spectrums including $^1$H-NMR, IR and MASS spectrums.

BEST MODE FOR CARRYING OUT THE INVENTION

On the pages that follow, the invention is described in greater detail by reference to examples. The invention is by no means limited to the following examples and the kinds of the compounds represented by formulas (1)–(3) and the solvent, as well as the kind of the bases to be used, etc. can be freely changed without departing from the scope and spirit of the invention.

Note that the sodium salt 2.5 hydrate of (5R,6S)-6-((R)-1-hydroxyethyl)-7-oxo-3-((R)-2-tetrahydrofuryl)-4-thia-1-azabicyclo[3.2.0]hept-2-ene-2-carboxylate which was used as a starting material in the examples and the comparative example that follow was prepared in accordance with the method described in JP 63-162694 A.

EXAMPLE 1

Production of (5-methyl-2-oxo-1,3-dioxolen-4-yl)methyl (5R,6S)-6-((R)-1-hydroxyethyl)-7-oxo-3-((R)-2-tetrahydrofuryl)-4-thia-1-azabicyclo[3.2.0]hept-2-ene-2-carboxylate

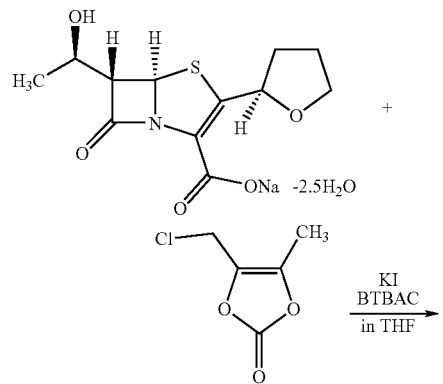

-continued

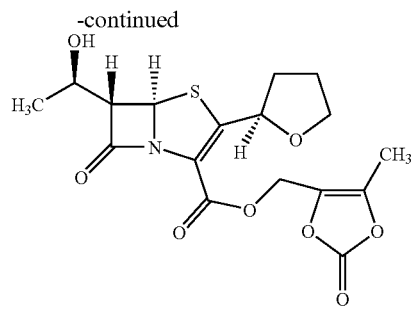

A weight (17.9 g) of sodium salt 2.5 hydrate of (5R,6S)-6-((R)-1-hydroxyethyl)-7-oxo-3-((R)-2-tetrahydrofuryl)-4-thia-1-azabicyclo[3.2.0]hept-2-ene-2-carboxylate (purity: 98.05%), potassium iodide (2.08 g), sodium hydrogencarbonate (0.84 g) and BTBAC (1.56 g) were mixed in THF (150 ml); to the mixture, 17.02 g of 4-chloromethyl-5-methyl-2-oxo-1,3-dioxolene (purity: 93.3%) was added and agitation was effected at 30° C. for 2 hours, then at 55° C. for 3 hours. After the end of the reaction, the reaction mixture was washed once with 50 ml of water and twice with 50 ml of 20% aqueous sodium chloride adjusted to pH=8 with sodium hydrogencarbonate; thereafter, the organic layer was concentrated under reduced pressure to give a mixture of the desired product and impurities. The obtained mixture was subjected to quantitative analysis by liquid chromatography using acetophenone as an internal standard material; the end product was obtained in a yield of 99.11%.

EXAMPLE 2

Production of (5-methyl-2-oxo-1,3-dioxolen-4-yl)methyl (5R,6S)-6-((R)-1-hydroxyethyl)-7-oxo-3-((R)-2-tetrahydrofuryl)-4-thia-1-azabicyclo[3.2.0]hept-2-ene-2-carboxylate

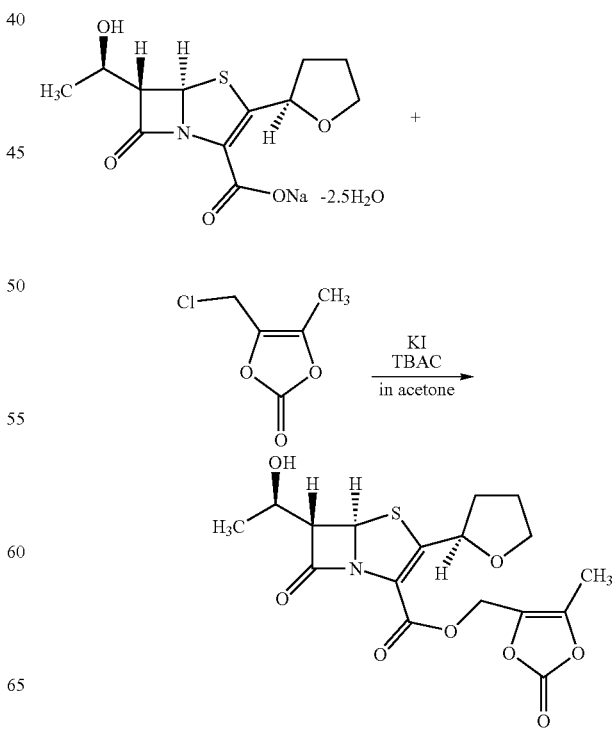

A weight (8.95 g) of sodium salt 2.5 hydrate of (5R,6S)-6-((R)-1-hydroxyethyl)-7-oxo-3-((R)-2-tetrahydrofuryl)-4-thia-1-azabicyclo[3.2.0]hept-2-ene-2-carboxylate (purity: 98.4%), potassium iodide (0.51 g), sodium hydrogencarbonate (0.21 g) and TBAC (0.40 g) were mixed in acetone (25 ml); to the mixture, 4.13 g of 4-chloromethyl-5-methyl-2-oxo-1,3-dioxolene (purity: 97.2%) was added and agitation was effected at 50° C. for 4 hours to perform the reaction. After filtering the reaction mixture to separate the inorganic salts insoluble in acetone, the solvent was distilled off under reduced pressure to obtain a mixture of the desired product and impurities. The obtained mixture was subjected to quantitative analysis by liquid chromatography using acetophenone as an internal standard material; the desired product was obtained in a yield of 94.2%.

COMPARATIVE EXAMPLE 1

Production of (5-methyl-2-oxo-1,3-dioxolen-4-yl)methyl (5R,6S)-6-((R)-1-hydroxyethyl)-7-oxo-3-((R)-2-tetrahydrofuryl)-4-thia-1-azabicyclo[3.2.0]hept-2-ene-2-carboxylate

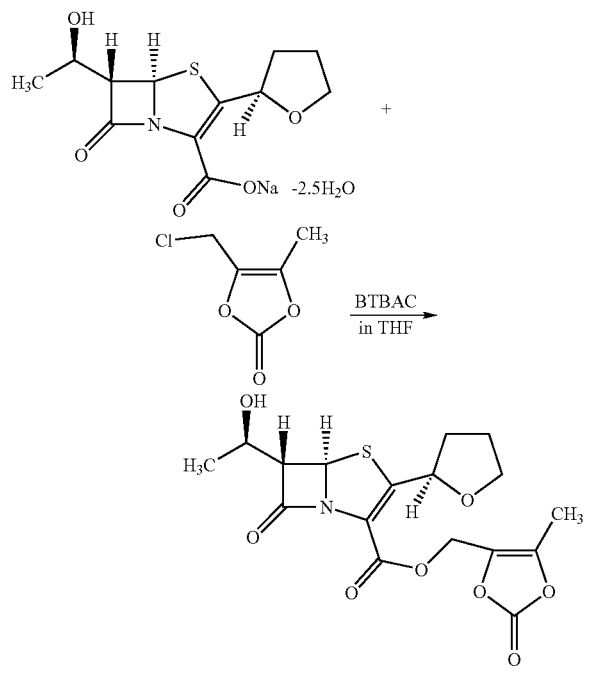

A weight (17.9 g) of sodium salt 2.5 hydrate of (5R,6S)-6-((R)-1-hydroxyethyl)-7-oxo-3-((R)-2-tetrahydrofuryl)-4-thia-1-azabicyclo[3.2.0]hept-2-ene-2-carboxylate (purity: 98.4%), sodium hydrogencarbonate (0.42 g) and BTBAC (0.78 g) were mixed in THF (75 ml); to the mixture, 8.25 g of 4-chloromethyl-5-methyl-2-oxo-1,3-dioxolene (purity: 97.2%) was added and agitation was effected at 50° C. for 4 hours to perform the reaction. After the end of the reaction, the reaction mixture was filtered to separate the inorganic salts insoluble in THF and the filtrate was concentrated under reduced pressure to obtain a mixture of the desired product and impurities. The obtained mixture was subjected to quantitative analysis by liquid chromatography using acetophenone as an internal standard material; the desired product was obtained in a yield of 36.7%.

INDUSTRIAL APPLICABILITY

As described above, according to the present invention, (dioxolenon-4-yl)methyl ester derivatives can be produced at low cost, in a simple manner, and at high yield.

In addition, the production process of the invention can be performed under comparatively mild reaction conditions and post-treatments after the end of the reaction are simple to perform. Therefore, the present invention can be applied advantageously to the case where compounds such as β-lactam antimicrobial agents that contain asymmetric carbons in the molecule are manufactured at an industrial production scale.

What is claimed is:
1. A process for producing a (dioxolenon-4-yl)methyl ester derivative of formula (3)

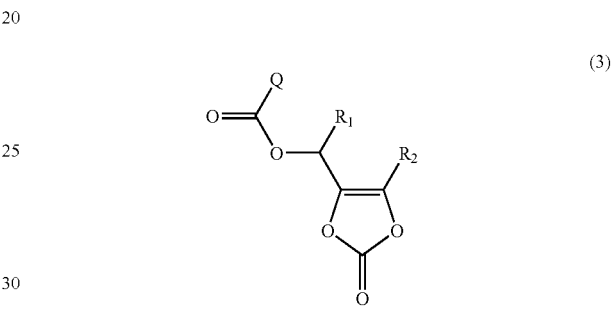

(where Q represents the fused heterocyclic group having a β-lactam ring of the following formulae:

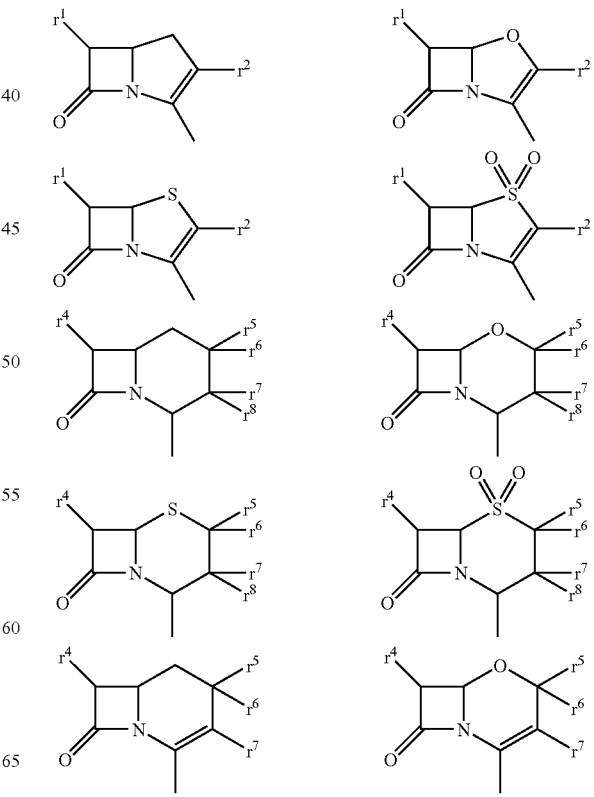

-continued

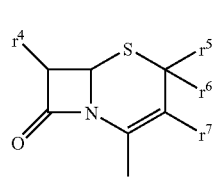 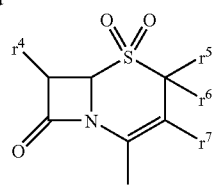

where $r^1$ and $r^4$ represent a 1-hydroxyethyl group or an optionally substituted benzoylamino group; $r^2$, $r^{5}$, $r^6$, $r^7$ and $r^8$ each independently represent hydrogen or a $C_{1-6}$ alkyl group that may be optionally substituted by $G^1$; a $C_{2-6}$ alkenyl group that may be optionally substituted by $G^1$; a $C_{2-6}$ alkynyl group that may be optionally substituted by $G^1$; a tetrahydrofuranyl and a heterocyclic group that may optionally be substituted by $G^1$;

$G^1$ represents a nitro group; a cyano group; a halogen atom; a $C_{1-6}$ alkoxy group; a $C_{1-6}$ alkylthio group; a $C_{1-6}$ alkylsulfinyl group; a $C_{1-6}$ alkylsulfonyl group; a $C_{1-6}$ alkylamino group; a di-$C_{1-6}$ alkylamino group; a $C_{1-6}$ alkylcarbonyl group; a $C_{1-6}$ alkoxycarbonyl group; an optionally $G^2$ substituted phenylsulfinyl group; an optionally $G^2$ substituted phenylsulfonyl group; an optionally $G^2$ substituted phenylthio group;

$G^2$ represents a halogen atom; a $C_{1-6}$ alkyl group; a $C_{1-6}$ haloalkyl group; or a $C_{1-6}$ haloalkoxy group; and $R_1$ and $R_2$ each independently represent a hydrogen atom, an optionally substituted $C_{1-6}$ alkyl group or an optionally substituted phenyl group, provided that $R_1$ and $R_2$ may combine to form an optionally substituted ring having 3–8 carbon atoms) by reacting a carboxylic acid derivative of formula (1)

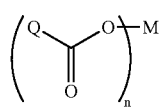

(1)

(where Q has the same meaning as defined above, M represents a hydrogen atom, an alkali metal, an alkaline earth metal or a transition metal, and n represents the atomic valency of M)

with a 4-chloromethyldioxolenone compound of formula (2)

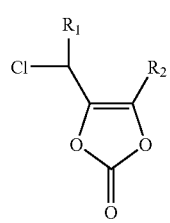

(2)

(where $R_1$ and $R_2$ have the same meanings as defined above) in a solvent in the presence of both a phase transfer catalyst and a metal iodide.

2. A process for producing a (dioxolenon-4-yl)methyl ester derivative of formula (3)

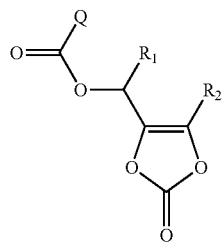

(3)

(where Q represents the fused heterocyclic group having a β-lactam ring of the following formulae:

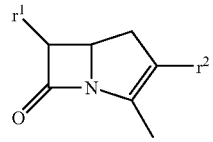

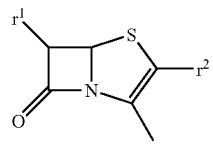

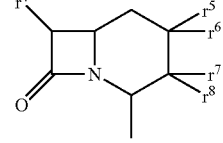

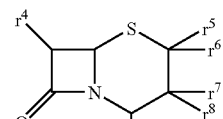

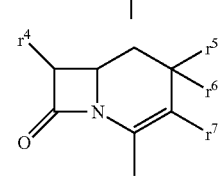

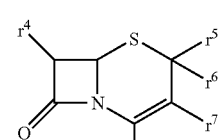

where $r^1$ and $r^4$ represent a 1-hydroxyethyl group or an optionally substituted benzoylamino group; $r^2$, $r^5$, $r^6$, $r^7$ and r8 each independently represent hydrogen or a $C_{1-6}$ alkyl group that may be optionally substituted by $G^1$; a $C_{2-6}$ alkenyl group that may be optionally substituted by $G^1$; a $C_{2-6}$ alkynyl group that may be optionally substituted by $G^1$; a tetrahydrofuranyl and a heterocyclic group that may optionally be substituted by $G^1$;

$G^1$ represents a nitro group; a cyano group; a halogen atom; a $C_{1-6}$ alkoxy group; a $C_{1-6}$ alkylthio group; a $C_{1-6}$ alkylsulfinyl group; a $C_{1-6}$ alkylsulfonyl group; a $C_{1-6}$ alkylamino group; a di-$C_{1-6}$ alkylamino group; a $C_{1-6}$ alkylcarbonyl group; a $C_{1-6}$ alkoxycarbonyl group; an optionally $G^2$ substituted phenylsulfinyl group; an optionally $G^2$ substituted phenylsulfonyl group; an optionally $G^2$ substituted phenylthio group;

$G^2$ represents a halogen atom; a $C_{1-6}$ alkyl group; a $C_{1-6}$ haloalkyl group; or a $C_{1-6}$ haloalkoxy group; and $R_1$ and $R_2$ each independently represent a hydrogen atom, an optionally substituted $C_{1-6}$ alkyl group or an optionally substituted phenyl group, provided that $R_1$ and $R_2$ may combine to form an optionally substituted ring having 3–8 carbon atoms)

by reacting a carboxylic acid of formula (5)

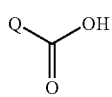

(5)

(where Q has the same meaning as defined above) with a 4-chloromethyldioxolenone compound of formula (2)

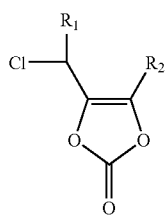

(2)

(where $R_1$ and $R_2$ have the same meanings as defined above) in a solvent in the presence of both a quaternary ammonium hydroxide of the formula: $R_aR_bR_cR_d$NOH (where $R_a$–$R_d$ each independently represent a $C_{1-20}$ alkyl group or a $C_{7-20}$ aralkyl group) and a metal iodide.

3. The process for producing a (dioxolenon-4-yl)methyl ester derivative of formula (3) according to claim 1 or 2, wherein a polar solvent is used as said solvent.

4. The process for producing a (dioxolenon-4-yl)methyl ester derivative of formula (3) according to any one of claims 1–2, wherein said metal iodide is used in an amount of 5–20 mol % of the 4-chloromethyldioxolenone compound of said formula (2).

5. The process for producing a (dioxolenon-4-yl)methyl ester derivative of formula (3) according to any one of claims 1–2, wherein an alkali metal iodide is used as said metal iodide.

6. The process for producing a (dioxolenon-4-yl)methyl ester derivative of formula (3) according to claim 1, wherein a quaternary ammonium salt is used as said phase transfer catalyst.

7. The process for producing a (dioxolenon-4-yl)methyl ester derivative of formula (3) according to claim 6, wherein a benzyltrialkylammonium halide is used as said quaternary ammonium salt.

8. The process for producing a (dioxolenon-4-yl)methyl ester derivative of formula (3) according to any one of claims 1–2, wherein a base is further added at least in an amount corresponding to the amount of the acidic impurities contained in the 4-chloromethyldioxolenone compound represented by said formula (2).

9. The process for producing a (dioxolenon-4-yl)methyl ester derivative of formula (3) according to any one of claims 1–2, wherein the reaction is performed by elevating the reaction temperature through a plurality of stages.

10. The process for producing a (dioxolenon-4-yl)methyl ester derivative of formula (3) according to claim 9, wherein the reaction is performed by elevating the reaction temperature in two stages, the first stage at 40° C. or below and the second stage at 50° C. or above.

11. The process for producing a (dioxolenon-4-yl)methyl ester derivative of formula (3) according to any one of claims 1–2, wherein the reaction is performed in a solvent selected from THF, DMF, DMSO or acetone.

12. The process for producing a (dioxolenon-4-yl)methyl ester derivative of formula (3) according to claim 11, wherein the solvent is THF.

* * * * *